United States Patent [19]

Mercado et al.

[11] Patent Number: 4,996,044

[45] Date of Patent: Feb. 26, 1991

[54] LIPSTICK FORMULATION AND METHOD

[75] Inventors: Clara G. Mercado, Aberdeen; Ann M. Krog, Red Bank, both of N.J.

[73] Assignee: Revlon, Inc., New York, N.Y.

[21] Appl. No.: 378,506

[22] Filed: Jul. 12, 1989

Related U.S. Application Data

[63] Continuation of Ser. No. 881,162, Jul. 2, 1986, abandoned, which is a continuation of Ser. No. 714,646, Mar. 21, 1985, abandoned.

[51] Int. Cl.$^5$ .............................................. A61K 7/025
[52] U.S. Cl. ...................................................... 424/64
[58] Field of Search ..................................... 424/64, 63

[56] References Cited

U.S. PATENT DOCUMENTS

| | | | |
|---|---|---|---|
| 3,574,822 | 4/1971 | Shepherd et al. | 424/63 |
| 3,911,105 | 10/1975 | Papantoniou | 424/64 |
| 3,937,811 | 2/1976 | Papantoniou et al. | 424/64 |
| 4,283,384 | 8/1981 | Jacquet et al. | 424/47 |
| 4,423,031 | 12/1983 | Murui et al. | 424/63 |
| 4,673,571 | 6/1987 | Mahieu et al. | 424/70 |

FOREIGN PATENT DOCUMENTS 2105727   3/1983   United Kingdom .

OTHER PUBLICATIONS

Yokota et al., cited in Chem. Abst. vol. 92, 1980, 64542k.

Balsam et al, eds. Cosmetics: Science and Technology, vol. 1, "Lipsticks", pp. 370–375, 378, 379, 1972.

*Primary Examiner*—John W. Rollins

[57] ABSTRACT

An improved lipstick formulation is provided which is creamy, shiny and soft, which includes relatively small amounts of organic high staining dyes and yet maintains its structural integrity and has excellent color laydown and long wear properties and includes an acrylates copolymer powder together with conventional lipstick ingredients.

8 Claims, No Drawings

LIPSTICK FORMULATION AND METHOD

This is a continuation, of application Ser. No. 06/881,162 filed 7/2/86, which is CIP of application Ser. No. 06/714,646, filed 3/21/85, both abandoned.

FIELD OF THE INVENTION

The present invention relates to a new lipstick formulation which includes relatively small amounts of organic staining dyes and yet has unique color laydown and long wear properties and good stick structure primarily due to the presence therein of a non-water dispersible acrylates copolymer powder.

BACKGROUND OF THE INVENTION

Lipsticks have been used for many years to impart color to the lips. The color helps to define the mouth area while imparting cosmetic shades that are suitable with fashion trends. Such lipsticks, in general, are made of an oily vehicle comprising fat or oil stiffened to a desired consistency with waxes of various types which also serve to raise the melting point and improve the physical stability. The color is ordinarily provided by insoluble pigments such as lakes of dye finely dispersed in the oily vehicle and one or more fluorescein dye derivatives which serve to stain the lips. A solvent for the dye is also included for increasing the effectiveness of this staining on the lips.

In recent years, attempts have been made to provide a lipstick which will impart a uniform long-lasting coloring to the lips and thus lessen the need for frequent reapplication. This has been accomplished by increasing the concentration of the dye and pigment in the conventional lipstick formulation to greater than 10% by weight. However, lipsticks containing such high concentrations of dye and pigment have been found to impart a dry non-uniform "cakey" look to the lips. This is particularly undesirable since current fashion trends are directed to producing a "wet" or "moist" look on the mouth. As a result, emollients, lubricants, and moisturizers are added in increased amounts to counteract the "cakey" results of the high dye and pigment containing lipstick formulations. However, these materials may impart a soft mushy easily breakable structure to the lipstick. Furthermore, these materials themselves are usually short-lived on the mouth since they are mechanically removed. In addition, these materials tend to act as vehicles for the dyes and pigments causing "creeping" or "feathering" on the outer edges of the mouth. This eliminates the sharp line of definition of the mouth area for which the product is applied.

Another approach to improving wear properties of lipstick has been to employ high staining organic dyes, for example, Red 21,14032, Orange 5,3655 and others. Unfortunately, it has been found that when high staining organic dyes are used in concentrations greater than 0.5% by weight of the lipstick, to achieve longer color wear, the stick structure of the lipstick is decreased in strength to an unsatisfactory level. Where it has been attempted to use the high staining organic dyes in amounts less than 0.5% by weight of the lipstick, it has not been possible to achieve the desired longer color wear.

DESCRIPTION OF THE INVENTION

In accordance with the present invention, a new creamy soft lipstick formulation is provided which has excellent laydown properties so that it may impart uniform long-lasting coloring to the lips, has excellent structural integrity properties so it will not easily break or become mushy, but stays intact, and has excellent color wear properties and stick strength even though it may include relatively small amounts of high staining dyes. Furthermore, the lipstick formulation of the invention does not contain inordinately high amounts of pigment and/or dye, so that it will not impart an undesirable dry "cakey" look to the lips. The improved laydown properties of the lipstick formulation of the invention is achieved, in part, through the inclusion of an acrylates copolymer powder therein.

With the enhanced lipstick formula of the invention containing acrylates copolymer, smaller concentrations of high staining organic dyes (that is, less than 0.5% based on the total weight of the lipstick), can be used to give the same result at higher concentrations (0.5% to 1%), thus giving longer wear and while maintaining good stick structure. In fact, it has been found that, in accordance with the present invention, even if high staining organic dyes are employed in amounts greater than 0.5%, longer color wear is achieved without sacrificing strength of stick structure.

The terms "high-staining organic dyes" and organic "high-staining dyes" are used interchangeably herein.

The lipstick formulation of the invention is anhydrous, that is, is free of water (and also free of alcohols), and is formed of from about 40 to about 80% and preferably from about 50 to about 70% by weight of anhydrous base intermediate which will be fully described hereinafter; from about 8 to about 35% by weight and preferably from about 12 to about 30% by weight of color intermediate comprised of a mixture of pigments or colors, which include from about 0.1 to about 3% and preferably from about 0.2 to about 0.9% by weight organic high staining dyes based on the weight of the color intermediate (or from about 0.03 to about 1% and preferably from about 0.07 to about 0.3% by weight organic high staining dyes based on weight of the lipstick formulation) which imparts enhanced long wear properties, and from about 3 to about 20% by weight and preferably from about 5 to about 15% by weight of one or more dispersing oils for organic pigments, optionally antioxidant and optionally preservative; from about 0.5 to about 5% by weight and preferably from about 1 to about 3% by weight of an acrylates copolymer intermediate, which imparts creaminess, shininess, superior color laydown properties, improved color wear and excellent structural integrity and stick strength even with the presence of the organic staining dyes, which acrylates copolymer intermediate includes from about 0.1 to about 4% and preferably from about 0.2 to about 2.5% by weight of the acrylates copolymer itself to impart and enhance color laydown properties and thus long wear of the formulation and an oil dispersant therefor; and optionally from about 0 to about 1% and preferably from about 0.1 to about 0.8% by weight fragrance, unless otherwise indicated, all of the above % being based on the total lipstick formulation.

The acrylates copolymer intermediate will generally be formed of from about 20 to about 80% by weight of a non-water dispersible acrylates copolymer powder and from about 80 to about 20% by weight of one or more oil dispersants therefor, such as castor oil, mineral oil, oleyl alcohol, liquid lanolin, sesame oil, isopropyl myristate, isopropyl palmitate, squalene and the like, with castor oil being preferred.

The acrylates copolymer powder will have the general formula

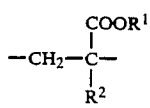

wherein $R^1$ is lower alkyl or hydrogen and $R^2$ is hydrogen or lower alkyl, and will have an average molecular weight of within the range of from about 100,000 to about 1,000,000. The powder will have an average particle size of within the range of from about 270 to about 325 mesh.

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the various branched chain isomers thereof.

Examples of such acrylates copolymers suitable for use herein include but are not limited to

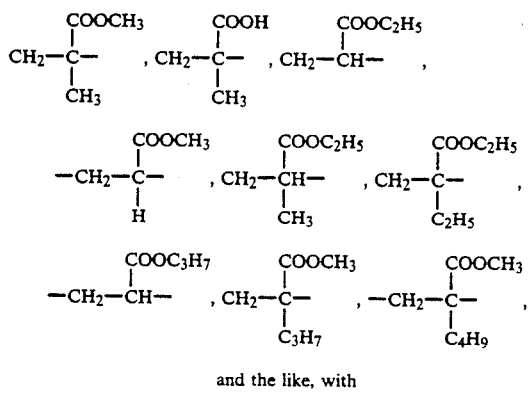

and the like, with

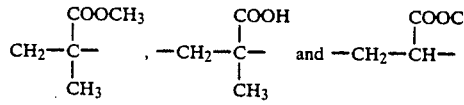

being preferred.

A most preferred acrylate copolymer powder is Polytrap 249 polymer powder which has the formula

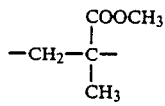

which has an average molecular weight within the range of from about 100,000 to about 500,000 and is marketed by Wickhen Products, Incorporated, Chemical Specialty Products, Huguenot, New York and has a bulk density of from about 0.52 to about 0.57, a flash point of greater than 300° F. and a particle size so that about 30% is retained on a 270 mesh screen and about 4% is retained on a 325 mesh screen.

The anhydrous base intermediate will generally be formed of one or more external stick strengtheners in an amount of within the range of from about 5 to about 20% by weight and preferably from about 8 to about 16% by weight based on the weight of the total lipstick formulation. Such external stick strengtheners provide one or more of the following properties: impart structural integrity to the lipstick, provide hardness, provide mold release properties, and stick strength and drag on the lips. Examples of external stick strengtheners suitable for use herein include waxes such as candelilla, ozokerite, carnauba, beeswax, cetyl alcohol, stearyl alcohol, super wool wax (a lanolin alcohol fraction), glyceryl monostearate and the like or mixture of two or more of such waxes.

One or more wax feel enhancers and structure strengtheners will also be included in the base intermediate in an amount within the range of from about 5 to about 20% by weight and preferably from about 9 to about 16% by weight of the total lipstick formulation. Examples of such wax feel enhancers and structure strengtheners include cetyl alcohol, stearyl alcohol, lanolin USP, super wool wax (a lanolin alcohol fraction), glyceryl monostearate and the like or mixtures thereof.

The base intermediate will also contain an internal stick strengthener in an amount within the range of from about 0.5 to about 10% by weight and preferably from about 1 to about 6% by weight based on the total stick formulation. A preferred internal stick strengthener is paraffin wax. Other examples are ozokerite wax or carnauba wax.

One or more feel enhancers for creamy feel will also be included in the base intermediate in an amount within the range of from about 1 to about 10% by weight and preferably from about 2 to about 7% by weight based on the total stick formulation. Examples of suitable enhancers for creamy feel include hydrogenated vegetable oil, isopropyl lanolate, synthetic cocoa butter, acetylated lanolin alcohol and lanolin derivatives or mixtures thereof.

One or more oils may be present which function as lip moisturizers, emollients, lubricants and/or glide or slip agents, such as petrolatum white (which is a slip moisturizer), oleyl alcohol (a penetrant), castor oil, low viscosity mineral oils (which are glide or slip agents, emollients and/or moisturizers), liquid lanolin, and/or jojoba oil (which are shine enhancers), isopropyl myristate, isopropyl palmitate, squalene and/or sesame oil (which are lubricants), and the like will also be present in the base intermediate in amounts within the range of from about 3 to about 30% by weight and preferably from about 5 to about 25% by weight based on the total weight of the stick formulation. It is preferred to employ a mixture of these oils for their different functions.

A coupling agent for waxes and oils will also be present in the anhydrous base intermediate in an amount within the range of from about 6 to about 20% by weight and preferably from about 8 to about 15% by weight of the total formulation. Examples of suitable coupling agents include oleyl alcohol, dipropyl dipelargonate or castor oil or mixtures thereof.

The base intermediate may optionally include one or more preservatives in amounts of within the range of from 0 to about 1.5% by weight and preferably from about 0.05 to about 0.3% by weight, and more preferably less than about 0.2% by weight of the total lipstick formulation, such as propyl p-hydroxybenzoate (propyl paraben), methyl p-hydroxybenzoate (methyl paraben), butyl p-hydroxybenzoate (butyl paraben), with propyl paraben being preferred; and optionally less than about 0.05% by weight of an antioxidant such as butylated hydroxyanisole or Vitamin E tocopherol, and other moisturizers such as wheat germ glycerides and hydrolyzed animal protein.

The term "hydrolyzed animal protein" as employed herein is as defined in U.S. Pat. No. 4,374,766 and refers to hydrolyzed collagen-derived animal protein having a molecular weight of within the range of from about 100 to about 200,000 and containing various amino acids including glycine, alanine, serine, threonine, proline, hydroxyproline, valine, isoleucine, phenylalanine, tyrosine, cystine/cysteine, methionine, aspartic acid, glutamic acid, arginine, histidine, lysine and hydroxylysine. Among the preferred hydrolyzed animal protein materials suitable for use herein are the collagen hydrolysates and derivatives referred to by the trademark CROTEINS manufactured by Croda, Inc., NYC., Umordant sold by Pentapharm, Inc., Super-Pro 100 sold by Stepan Chemical Co., Proto-Lan 20 sold by Maybrook Inc., Lexein X-250 sold by Inolex Corp., Lanasan Cl sold by Sandoz, Inc. and Peptein 2000 sold by Hormel. The Croda product is formed by hydrolyzing collagen (by alkali, acid or enzyme hydrolysis) and breaking the long collagen chains so that the molecular weight is reduced from the millions to hydrocolloids ranging from a molecular weight of 100 to 300,000 and preferably from 100 to 200,000. Amino acid composition of preferred collagen derived protein is set out below.

| Amino Acid | % Present |
| --- | --- |
| Glycine | 20.0–30.5 |
| Alanine | 8.0–11.0 |
| Serine | 2.9–4.1 |
| Threonine | 1.8–2.6 |
| Proline | 13.7–18.0 |
| Hydroxyproline | 12.1–14.5 |
| Valine | 2.1–3.4 |
| Isoleucine | 1.3–1.8 |
| Leucine | 2.8–3.5 |
| Phenylalanine | 1.1–2.6 |
| Tyrsine | 0.2–1.0 |
| Cystine/Cysteine | 0.0–0.9 |
| Methionine | 0.7–0.9 |
| Aspartic Acid | 5.7–9.0 |
| Glutamic Acid | 10.0–11.7 |
| Arginine | 7.8–9.0 |
| Histidine | 0.7–1.0 |
| Lysine | 3.9–5.2 |
| Hydroxylysine | 0.7–1.2 |

The term "wheat germ glycerides" as employed herein is as defined in the CTFA Cosmetic Ingredient Dictionary, Second Edition, 1977, namely, a mixture of mono-, di- and triglycerides produced by the transesterification of wheat germ oil. It is a known material and is available commercially as Wickenol 535 from Wickhen Products, Inc., Huguenot, N.Y. 12746.

The color intermediate will contain from about 25 to about 40% by weight and preferably from about 30 to about 36% by weight (based on the weight of the color intermediate) of one or more color pigments which include one or more organic high staining dyes, optionally one or more other organic dyes (including medium staining organic dyes and/or low staining organic dyes), and optionally one or more inorganic pigments (such as iron oxides), and from about 55 to about 75% by weight and preferably from about 60 to about 70% by weight of one or more color dispersants, such as castor oil, mineral oil, oleyl alcohol, liquid lanolin, sesame oil, isopropyl myristate, isopropyl palmitate, squalene, mixtures of two or more thereof, with castor oil being preferred, optionally less than about 0.05% and preferably less than about 0.03% by weight antioxidant, such as set out above with respect to the base intermediate, and optionally less than about 0.3% by weight and preferably less than about 0.2% by weight preservative, such as set out above with respect to the base intermediate, all of the above percentages being based on the total weight of the color intermediate.

The dyes employed in the formulation are the U. S. Government certified colors, both Drug and Cosmetic grade, and Food, Drug and Cosmetic grade. The organic high staining dyes will be employed in an amount within the range of from about 0.1 to about 3% and preferably from about 0.2 to about 0.9% by weight of the color intermediate, and the optional other organic dyes will be employed in an amount within the range of from about 0.5 to about 25% and preferably from about 1 to about 15% by weight of the color intermediate. Examples of such organic high staining dyes suitable for use herein include Red 21,14032, Orange 5,3655, Blue 1,7117 or other conventional organic high staining dyes approved for cosmetic use, or mixtures thereof. Examples of such other organic dyes suitable for use herein include medium-staining organic dyes such as Red 27,3127, Red 27,6527, Red 7,C19-025, and Red 33,7192 and low-staining organic dyes such as Red 27,7047, Red 7,K7183, Red 7,7044, Red 7,C19-011, Red 6,31-3006, Red 6,C19-012, Red 6,6906, Yellow 6,C70-5270, Yellow 5,69002, and Red 30, or other conventional organic dyes approved for cosmetic use, or mixtures thereof. The inorganic pigments may be employed in an amount within the range of from about 0 to about 30% and preferably from about 5 to about 20% by weight of the color intermediates. Inorganic pigments include iron oxides, titanium dioxide, iron sulfides, or other conventional inorganic pigments approved for cosmetic use.

As indicated, the presence of the organic high staining dyes imparts excellent color wear properties to the lipstick of the invention. However, it is the combination and presence of both the organic high staining dyes and the acrylates copolymer that impart both excellent color wear properties and stick strength as well as excellent color laydown.

Anhydrous natural flavor and fragrance oils such as peppermint oil, lemon oil, orange oil, etc. or synthetic flavor and fragrance oils may optionally be included in the lipstick formulation by incorporation into the anhydrous base or even into the color intermediate, in amounts of less than about 1% by weight of the lipstick formulation and preferably from about 0.1 to about 0.8% by weight.

The lipstick when applied coats the lips with the acrylate copolymer causing the color or pigment to easily laydown in a creamy uniform manner with the colors penetrating every pore and crevice on the lip surface.

Preferred lipstick formulations in accordance with the present invention are set out below.

| Preferred Formulations | |
| --- | --- |
| Ingredient | % w/w of Total Lipstick Formulation |
| Base Intermediate | 50 to 70 |
| Candelilla wax (stick strengthener) | 10 to 14 |
| Cetyl alcohol (feel enhancer) | 2 to 6 |
| Ozokerite (paraffin wax - hardness internal stick strengthener) | 1.5 to 10 |
| Lanolin alcohol (feel enhancer) | 7 to 20 |

Preferred Formulations

| Ingredient | % w/w of Total Lipstick Formulation |
| --- | --- |
| Beeswax (strengthener) | 0.5 to 5 |
| Hydrogenated vegetable oil (feel enhancer-cream) | 3 to 6 |
| Petrolatum white (lip moistener) | 1.5 to 12 |
| Lanolin oil (shine enhancer) | 4 to 8 |
| Mineral oil (glide or slip agent) | 4 to 8 |
| Oleyl alcohol (coupling agent for wax and oils) | 7 to 15 |
| Preservative | 0 to 0.1 |
| Antioxidant | 0 to 0.02 |
| Color Intermediate | 10 to 35 |
| Pigments and castor oil dispersant (1:4 to 1:1) (Pigments and dyes - organic high staining dyes (0.2 to 0.9%) other organic dyes (1 to 20%) inorganic pigments (0 to 20%)) (All of above based on total weight of color intermediate) | 20 to 30 |
| Antioxidant | 0 to 0.01 |
| Preservative | 0 to 0.05 |
| Softener (castor oil) | 6 to 20 |
| Acrylates Copolymer Phase Acrylates copolymer Dispersant (castor oil) (1:4 to 4:1) | 1 to 3 |
| Fragrance | 0.1 to 0.8 |

The lipstick formulation of the invention may be prepared by forming a mixture of the anhydrous base intermediate ingredients wherein the waxes, oil and other ingredients are heated to 80°–85° C. with agitation until a liquid is formed (uniform). Next the softener or dispersant (for example, castor oil) is added with propeller mixing maintaining a temperature 70°–75° C.

The color intermediate phase (formed by adding the color to the dispersant, heating with agitation at 65° to 75° C. and then roller milling three times) is added to the base intermediate-softener phase with mixing for 40 to 80 minutes.

Next, the acrylates copolymer intermediate (formed by adding the copolymer to the dispersant and roller milling 3 times) is added to the mix and mixing is continued for 20 to 35 minutes until a uniform mixture is obtained. Fragrance (where present) is then added and mixing is continued for 10 minutes while maintaining heating at 70° to 75° C.

The mixture is then molded to form the lipstick formulation of the invention.

The following Examples represent preferred embodiments of the present invention.

EXAMPLE 1

A lipstick formulation having the following composition was prepared as described below.

| Ingredient | Parts by Weight |
| --- | --- |
| Base intermediate | 60 |
| Candelilla wax | 12 |
| Cetyl alcohol | 4 |
| Ozokerite | 2.3 |
| Lanolin alcohol | 9.2 |
| Beeswax | 5 |
| Hydrogenated vegetable oil | 2.5 |
| Petrolatum white | 6.4 |
| Lanolin oil | 6.4 |
| Oleyl alcohol | 11.6 |
| Propyl paraben | 0.09 |
| Butylated hydroxyanisole | 0.02 |
| Softener-castor oil | 7.46 |
| Color intermediate | |
| Red 7 | 4 |
| Russet | 2.5 |
| Red 6 | 1 |
| TiO$_2$ | 2 |
| Castor oil | 20 |
| Propyl paraben | 0.005 |
| Butylated hydroxyanisole | 0.025 |
| Acrylates Copolymer Intermediate | |
| Acrylates copolymer (Polytrap 249 polymer powder) | 1.5 |
| Castor oil | 1.5 |
| Fragrance | 0.5 |

1. All of the waxes were melted in a steam-jacketed kettle with propeller mixer agitation while maintaining the temperature at from 75° to 85° C. After the waxes were melted, the oil components except for the castor oil and the remaining components of the base intermediate were added and agitation was continued.

2. The dyes, pigments, preservative and antioxidant were added to the castor oil in a separate kettle and heated with agitation at 70° C. Agitation was continued until a proper dispersion achieved. The dispersion of oil and coloring agent were passed through a three-roll mill. The color dispersion was added to the base intermediate with mixing for 40 to 60 minutes.

3. The acrylates copolymer dispersed in castor oil and roller milled three times was added to the above mixture with mixing for 20 to 30 minutes until a uniform mixture was obtained.

4. Fragrance was then added with mixing for 10 minutes.

The resulting lipstick formulation was poured into molds and taken to freezing temperatures to form the lipstick.

It was found that the lipstick formulation of the invention incorporating the acrylates copolymer powder was soft but had good structure, was creamy, shiny and had excellent color laydown for long wear properties.

EXAMPLE 2

Following the procedure of Example 1, a lipstick formulation was prepared having the following composition.

| Ingredient | Parts by Weight |
| --- | --- |
| Base intermediate (48 parts) | |
| Candelilla wax | 9.2 |
| Ozokerite | 4.5 |
| Lanolin alcohol | 9.2 |
| Acetylated lanolin alcohol | 7 |
| Hydrolyzed animal protein | 0.25 |
| Petrolatum white | 9.2 |
| Wheat germ glycerides | 0.45 |
| Vitamin E (dl-alpha tocopherol) | 0.03 |
| Oleyl alcohol | 8 |
| Propyl paraben | 0.2 |
| Softener-castor oil | 19.14 |
| Color intermediate | |
| Red 7 | 4 |
| Russet | 2.5 |
| Red 6 | 1 |

-continued

| Ingredient | Parts by Weight |
|---|---|
| TiO$_2$ | 2 |
| Castor oil | 20 |
| Propyl paraben | 0.005 |
| Butylated hydroxyanisole | 0.025 |
| Acrylates Copolymer Intermediate | |
| Acrylates copolymer (Polytrap 249 polymer powder) | 1.5 |
| Castor oil | 1.5 |
| Fragrance | 0.3 |

It was found that the lipstick formulation of the invention incorporating the acrylates copolymer powder was soft but had good structure, was creamy, shiny and had excellent color laydown.

EXAMPLE 3

A lipstick formulation having the following composition containing high staining organic dyes was prepared as described below.

| Ingredient | | Parts by Weight of lipstick |
|---|---|---|
| *Base intermediate | | 65 |
| Softener | | 7.4 |
| Castor oil | | 2.0 |
| Lanolin oil | | 5.4 |
| Color intermediate | | 24.6 |
| Orange 5,3655 | high staining organic dyes | 0.07 |
| Red 21,14032 | | 0.07 |
| Red 6,C19-028 | 6.3 other pigments and organic dyes | |
| Pink 3571 | | 0.4 |
| Red 7,7044 | | 0.9 |
| Yellow 6,5270 | | 0.4 |
| Castor oil | | 16.5 |
| Propyl paraben | | 0.005 |
| Butylated hydroxyanisole | | 0.025 |
| Acrylates Copolymer Intermediate | | |
| Acrylates copolymer (Polytrap 249 polymer powder) | | 1.8 |
| Castor oil | | 0.9 |
| Fragrance | | 0.3 |
| *Base Intermediate | | % by Weight of Base Intermediate |
| Candelilla wax | | 20 |
| Cetyl alcohol | | 6.7 |
| Ozokerite | | 3.8 |
| Lanolin alcohol | | 15.3 |
| Beeswax | | 1.4 |
| Hydrogenated vegetable oil | | 8 |
| Petrolatum white | | 4 |
| Lanolin oil | | 10.7 |
| Mineral oil | | 9.2 |
| Oleyl alcohol | | 19.4 |
| Propyl paraben | | 0.2 |
| Wheat germ glycerides | | 1 |
| Hydrolyzed animal protein | | 0.5 |
| Vitamin E, dl-alpha tocopherol | | 0.05 |

1. All of the waxes were melted in a steam-jacketed kettle with propeller mixer agitation while maintaining the temperature at from 75° to 80° C. After the waxes were melted, the oil components (softener) and the remaining components of the base intermediate were added and agitation was continued.

2. The dyes, pigments, preservative and antioxidant were added to the castor oil in a separate kettle and heated with agitation at 70°-75° C. Agitation was continued until a proper dispersion achieved. The dispersion of oil and coloring agent were passed through a three-roll mill. The color dispersion was added to the base intermediate with mixing for 40 to 80 minutes.

3. The acrylates copolymer dispersed in castor oil and roller milled three times was added to the above mixture with mixing for 20 to 30 minutes until a uniform mixture was obtained.

4. Fragrance was then added with mixing for 10 minutes.

The resulting lipstick formulation was poured into molds and taken to freezing temperatures to form the lipstick.

It was found that the lipstick formulation of the invention incorporating the acrylates copolymer powder was soft but had good structure, was creamy, shiny and had excellent color laydown for long wear properties.

EXAMPLE 4

Following the procedures of Example 3, a lipstick formulation was prepared having the following composition.

| Ingredient | | Parts by Weight |
|---|---|---|
| Base intermediate (as per Ex. 3) | | 65 |
| Softener | | 5.2 |
| Castor oil | | 3.2 |
| Lanolin oil | | 2 |
| Color intermediate | | |
| Red 21,14032 - organic high staining dye | | 0.17 |
| Russett C33-2527 | other pigments and organic dyes | 0.6 |
| Red 33,K7192 | | 0.3 |
| Red 7,7044 | | 1.3 |
| DC Red 6,C19-012 (barium lake) | | 1.1 |
| Red 27,704 | | 1.7 |
| TiO$_2$ | | 3.9 |
| Castor oil | | 18 |
| Propyl paraben | | 0.005 |
| Butylated hydroxyanisole | | 0.025 |
| Acrylates Copolymer Intermediate | | 2.7 |
| Acrylates copolymer (Polytrap 249 polymer powder) | | 1.8 |
| Castor oil | | 0.9 |
| Fragrance | | 0.3 |

It was found that the lipstick formulation of the invention incorporating the acrylates copolymer powder was soft but had good stick structure, was creamy, shiny and had excellent color laydown for long wear properties.

What is claimed is:

1. A lipstick formulation comprising 50-70% of a base intermediate, containing by weight of the total composition, 10-14% candelilla wax, 2-6% cetyl alcohol, 1.5-10% ozokerite, 7-20% lanolin alcohol, 0.5-5% beeswax, 3-6% hydrogenated vegetable oil, 1.5-12% petrolatum white, 4-8% lanolin oil, 4-8% mineral oil, and 7-15% oleyl alcohol; 10-35% of a color intermediate, containing by weight of the total composition, 20-30% pigments and castor oil dispersant in a range of 1:4 to 1:1 wherein the pigments are 0.2-0.9% based upon total weight of color intermediate, of organic high staining dyes, and 1-20% based upon total weight of color intermediate of organic dyes; 6-20% by weight of the total composition of castor oil; 1-3% by weight of the total composition of acrylates copolymer dispersant in a range of 1:4 to 4:1; and 0.1-0.8% by weight of the total composition of fragrance.

2. The formulation of claim 1 wherein the base intermediate additionally contains up to 0.01% antioxidant and up to 0.05% preservative.

3. The formulation of claim 2 wherein the color intermediate additionally contains up to 20% based upon total weight of color intermediate of inorganic pigments.

4. The formulation of claim 3 wherein the acrylates copolymer dispersant is castor oil.

5. A lipstick composition of the formula:

| Ingredient | Parts by Weight. |
|---|---|
| Base intermediate | 60 |
| Candelilla wax | 12 |
| Cetyl alcohol | 4 |
| Ozokerite | 2.3 |
| Lanolin alcohol | 9.2 |
| Beeswax | 5 |
| Hydrogenated vegetable oil | 2.5 |
| Petrolatum white | 6.4 |
| Lanolin oil | 6.4 |
| Oleyl alcohol | 11.6 |
| Propyl paraben | 0.09 |
| Butylated hydroxyanisole | 0.02 |
| Softener-castor oil | 7.46 |
| Color intermediate | |
| Red 7 | 4 |
| Russet | 2.5 |
| Red 6 | 1 |
| TiO$_2$ | 2 |
| Propyl paraben | 0.005 |
| Butylated hydroxyanisole | 0.025 |
| Acrylates Copolymer Intermediate | |
| Acrylates copolymer | 1.5 |
| Castor oil | 1.5 |
| Fragrance | 0.5 |

6. A lipstick composition of the formula:

| Base intermediate (48 parts) | Parts by Weight |
|---|---|
| Candelilla wax | 9.2 |
| Ozokerite | 4.5 |
| Lanolin alcohol | 9.2 |
| Acetylated lanolin alcohol | 7 |
| Hydrolyzed animal protein | 0.25 |
| Petrolatum white | 9.2 |
| Wheat germ glycerides | 0.45 |
| Vitamin E (dl-alpha tocopherol) | 0.03 |
| Oleyl alcohol | 8 |
| Propyl paraben | 0.2 |
| Softener castor oil | 19.14 |
| Color intermediate | |
| Red 7 | 4 |
| Russet | 2.5 |
| Red 6 | 1 |
| TiO$_2$ | 2 |
| Castor oil | 20 |
| Propyl paraben | 0.005 |
| Butylated hydroxyanisole | 0.025 |
| Acrylates Copolymer Intermediate | |
| Acrylates Copolymer | 1.5 |
| Castor oil | 1.5 |
| Fragrance | 0.3 |

7. A lipstick composition of the formula:

| Ingredient | Parts by Weight |
|---|---|
| *Base intermediate | 65 |
| Softener | 7.4 |
| Castor oil | 2.0 |
| Lanolin oil | 5.4 |
| Color intermediate | 24.6 |
| Orange 5,3655 | 0.07 |
| Red 21,14032 | 0.07 |
| Red 6,C19-028 | 6.3 |
| Pink 3571 | 0.4 |
| Red 7,7044 | 0.9 |
| Yellow 6,5270 | 0.4 |
| Castor oil | 16.5 |
| Propyl paraben | 0.005 |
| Butylated hydroxyanisole | 0.025 |
| Acrylates Copolymer Intermediate | |
| Acrylates copolymer | 1.8 |
| Castor Oil | 0.9 |
| Fragrance | 0.3 |

| *Base Intermediate | % by Weight of Base Intermediate |
|---|---|
| Candelilla wax | 20 |
| Cetyl alcohol | 6.7 |
| Ozokerite | 3.8 |
| Lanolin alcohol | 15.3 |
| Beeswax | 1.4 |
| Hydrogenated vegetable oil | 8 |
| Petrolatum white | 4 |
| Lanolin oil | 10.7 |
| Mineral oil | 9.2 |
| Oleyl alcohol | 19.4 |
| Propyl paraben | 0.2 |
| Wheat germ glycerides | 1 |
| Hydrolyzed animal protein | 0.5 |
| Vitamin E, dl-alpha tocopherol | 0.05 |

8. A lipstick composition of the formula:

| Ingredient | Parts by Weight |
|---|---|
| *Base intermediate | 65 |
| Softener | 5.2 |
| Castor oil | 3.2 |
| Lanolin oil | 2 |
| Color intermediate | |
| Red 21,14032 | 0.17 |
| Russett C33-2527 | 0.6 |
| Red 33,K7192 | 0.3 |
| Red 7,7044 | 1.3 |
| D&C Red 6,C19-012 (barium lake) | 1.1 |
| Red 27,704 | 1.7 |
| TiO$_2$ | 3.9 |
| Castor oil | 18 |
| Propyl paraben | 0.005 |
| Butylated hydroxyanisole | 0.025 |
| Acrylates Copolymer Intermediate | 2.7 |
| Acrylates copolymer | 1.8 |
| Castor oil | 0.9 |
| Fragrance | 0.3 |

| *Base Intermediate | % by Weight of Base Intermediate |
|---|---|
| Candelilla wax | 20 |
| Cetyl alcohol | 6.7 |
| Ozokerite | 3.8 |
| Lanolin alcohol | 15.3 |
| Beeswax | 1.4 |
| Hydrogenated vegetable oil | 8 |
| Petrolatum white | 4 |
| Lanolin oil | 10.7 |
| Mineral oil | 9.2 |
| Oleyl alcohol | 19.4 |
| Propyl paraben | 0.2 |
| Wheat germ glycerides | 1 |

* * * * *